(12) United States Patent
Handa et al.

(10) Patent No.: US 8,852,555 B2
(45) Date of Patent: Oct. 7, 2014

(54) PROCESS FOR PRODUCTION OF SURFACE-COATED INORGANIC PARTICLES

(75) Inventors: Hiroshi Handa, Yokohama (JP); Mamoru Hatakeyama, Yokohama (JP); Masanori Abe, Tokyo (JP); Satoshi Sakamoto, Yokohama (JP); Yuka Masaike, Yokohama (JP); Kosuke Nishio, Yokohama (JP); Yoshinori Kita, Yokohama (JP); Hiroshi Kishi, Yokohama (JP)

(73) Assignee: Tokyo Institute of Technology, Tokyo (JP)

( * ) Notice: Subject to any disclaimer, the term of this patent is extended or adjusted under 35 U.S.C. 154(b) by 1018 days.

(21) Appl. No.: 12/670,807

(22) PCT Filed: Jul. 25, 2008

(86) PCT No.: PCT/JP2008/063361
§ 371 (c)(1),
(2), (4) Date: Mar. 18, 2010

(87) PCT Pub. No.: WO2009/014201
PCT Pub. Date: Jan. 29, 2009

(65) Prior Publication Data
US 2010/0254908 A1    Oct. 7, 2010

(30) Foreign Application Priority Data

Jul. 26, 2007   (JP) ................. P2007-194233

(51) Int. Cl.
| | | |
|---|---|---|
| *A61K 49/00* | (2006.01) | |
| *C09C 3/08* | (2006.01) | |
| *B22F 1/00* | (2006.01) | |
| *B82Y 30/00* | (2011.01) | |
| *A61K 49/18* | (2006.01) | |
| *C09C 1/24* | (2006.01) | |
| *C09C 3/10* | (2006.01) | |
| *G01N 33/543* | (2006.01) | |
| *B82Y 25/00* | (2011.01) | |
| *H01F 1/00* | (2006.01) | |
| *C09C 3/12* | (2006.01) | |
| *A61K 41/00* | (2006.01) | |

(52) U.S. Cl.
CPC .............. *H01F 1/0045* (2013.01); *G01G 49/00* (2013.01); *C09C 3/08* (2013.01); *B22F 1/0062* (2013.01); *B82Y 30/00* (2013.01); *A61K 49/1851* (2013.01); *C09C 1/24* (2013.01); *C09C 3/10* (2013.01); *B22F 1/0022* (2013.01); *G01N 33/54393* (2013.01); *A61K 49/1854* (2013.01); *A61K 49/1836* (2013.01); *B82Y 25/00* (2013.01); *A61K 49/1833* (2013.01); *C09C 3/12* (2013.01); *A61K 41/0052* (2013.01); *A61K 49/183* (2013.01); *C01P 2006/42* (2013.01)
USPC ............ 424/9.1; 424/9.35; 424/489; 424/490

(58) Field of Classification Search
USPC ............................ 424/489, 490, 9.1–9.3, 9.35
See application file for complete search history.

(56) References Cited

U.S. PATENT DOCUMENTS

| | | | |
|---|---|---|---|
| 5,928,958 | A | 7/1999 | Pilgrimm |
| 6,193,953 | B1 * | 2/2001 | Lohrmann et al. ........... 424/9.52 |
| 6,274,121 | B1 | 8/2001 | Pilgrimm |
| 6,361,944 | B1 * | 3/2002 | Mirkin et al. ................. 435/6.11 |
| 6,638,494 | B1 | 10/2003 | Pilgrimm |
| 6,797,380 | B2 | 9/2004 | Bonitatebus, Jr. et al. |
| 2006/0024235 | A1 | 2/2006 | Pilgrimm |
| 2008/0038361 | A1 | 2/2008 | Cheon et al. |
| 2008/0045770 | A1 * | 2/2008 | Sigmund et al. .............. 588/299 |

FOREIGN PATENT DOCUMENTS

| | | |
|---|---|---|
| EP | 1386886 A1 * | 2/2004 |
| JP | 10 503281 | 3/1998 |
| JP | 2000 507197 | 6/2000 |
| JP | 2004 75530 | 3/2004 |
| JP | 2006 502572 | 1/2006 |
| JP | 2006 282582 | 10/2006 |
| WO | 2006 025627 | 3/2006 |

OTHER PUBLICATIONS

Lattuada, Marco et al., "Functionalization of Monodisperse Magnetic Nanoparticles", Langmuir, vol. 23, No. 4, pp. 2158-5168, (Feb. 13, 2007).

(Continued)

*Primary Examiner* — Michael G Hartley
*Assistant Examiner* — Micah-Paul Young
(74) *Attorney, Agent, or Firm* — Oblon, Spivak, McClelland, Maier & Neustadt, L.L.P.

(57) ABSTRACT

Nano-sized inorganic particles having uniform particle sizes and precisely controlled particle diameters have already been produced by synthesis in an organic solvent, but these nano-sized inorganic particles are hindered from dispersing in a polar solvent because of the adsorption of a long-chain fatty acid on the surfaces of the particles. Further, it was difficult to form nano-sized inorganic particles dispersible in a polar solvent by replacing the long-chain fatty acid coats. According to the invention, various surface-coated inorganic particles dispersible in polar solvents can be produced from fatty acid-coated inorganic particles by adding a temporary coating substance such as thiomalic acid to a nonpolar solvent containing fatty acid-coated inorganic particles dispersed therein to replace the fatty acid coats by the temporary coating substance, dispersing the inorganic particles coated with the temporary coating substance in a polar solvent, and then adding a coating substance dispersible in a polar solvent, e.g., citric acid to the obtained dispersion to replace the temporary coating substance coats covering the inorganic particles by the coating substance dispersible in a polar solvent.

16 Claims, 3 Drawing Sheets

(56) References Cited

OTHER PUBLICATIONS

Sun, Yongkang et al., "An improved way to prepare superparamagnetic magnetite-silica core-shell nanoparticles for possible biological application", Journal of Magnetism and Magnetic Materials, Elsevier, vol. 285, pp. 65-70, (2005).

Jun, Young-wook et al., "Nanoscale Size Effect of Magnetic Nanocrystals and Their Utilization for Cancer Diagnosis via Magnetic Resonance Imaging", J. Am. Chem. Soc., vol. 127, No. 16, pp. 5732-5733, (2005).

Jiang, Wanquan et al., "Preparation and properties of superparamagnetic nanoparticles with narrow size distribution and biocompatible", Journal of Magnetism and Magnetic Materials, Elsevier, vol. 283, No. 6, pp. 210-214, (Dec. 2-3, 2004).

Sun, Shouheng et al., "Monodisperse $MFe_2O_4$ (M=Fe, Co, Mn) Nanoparticles", J. Am. Chem. Soc., vol. 126, No. 1, pp. 273-279, (2004).

Park, Jongnam et al., "Ultra-large-scale syntheses of monodisperse nanocrystals", Nature Materials, Letters, vol. 3, pp. 891-895, (Dec. 2004).

Chinese Office Action issued Feb. 24, 2012, in Patent Application No. 200880100656.3 (with English-language translation).

Yongkang Sun, et al., "Tunable synthesis of magnetic iron oxide nanoparticles and the related structures", Department of Biomedical Engineering, Southeast University, Key Laboratory of Molecular and Biomolecular Electronics, Jun. 2004, 98 pages (with English Abstract).

* cited by examiner

PROCESS FOR PRODUCTION OF SURFACE-COATED INORGANIC PARTICLES

CROSS REFERENCE TO RELATED APPLICATION

This application is a 371 of PCT/JP2008/063361, filed on Jul. 25, 2008, and claims priority to Japanese Patent Application No. 2007-194233, filed on Jul. 26, 2007.

TECHNICAL FIELD

The present invention relates to a process for production of surface-coated inorganic particles and the surface-coated inorganic particles. Particularly, the present invention relates to a process for production of surface-coated inorganic particles where the aliphatic acid covering of the surfaces of hydrophobic inorganic particles covered with aliphatic acid is substituted to obtain hydrophilic inorganic particles and to the surface-coated inorganic particle produced by the production process.

BACKGROUND ART

The technique for producing so-called nano-sized crystalline particles with respective sizes within a range of several nm to several hundred nm is developed so that nano-sized crystals for various materials can be produced in the state of monodispersity. Among them, when the inorganic particles made of metallic oxide are synthesized in an organic solvent, the inorganic particles which are finely controlled in particle size and are uniformed in particle diameter can be obtained under the state of monodispersity. Such fundamental researches and developments for nano-sized crystal are being intensely progressed and the thus obtained results are expected as the applications for various technical fields.

Non-patent Reference 1 (J. Am. Chem. Soc. 2004, 126, P. 273-279) has reported as one of applications the production process of nano-sized $Fe_3O_4$ particles. In the production process, ferric acetylacetonate complex salt is solved in a solvent mixed with oleic acid and 1,2-hexadecandic diol containing oleylamine and having high boiling point to obtain nano-sized $Fe_3O_4$ particles which are finely controlled in particle size and uniformed in particle diameter. Non-patent Reference 1 has also reported that cobalt and/or manganese acetylacetonate complex salt are contained in addition to the ferric acetylacetonate complex salt such that the iron (Fe) atoms of the nano-sized $Fe_3O_4$ particles are partially substituted with the cobalt atoms and/or the manganese atoms. According to these production processes, the intended nano-sized crystals can be finely controlled in particle size in an organic solvent. The well averaging in particle diameter is considered to be originated from that the corresponding nuclei are created simultaneously and the intended nano-size crystals are independently grown under almost the same condition as one another.

Non-patent Reference 2 (Nat. Mater. 2004, 3, P. 891-895) has reported that iron chloride and sodium oleate are reacted with one another to form iron oleate complex, which is solved in 1-octadecene containing oleic acid, increased slowly in temperature up to 320° C. and maintained at the same temperature for a predetermined period of time, thereby synthesizing a large amount of nano-sized crystalline $Fe_3O_4$ particles. The nano-sized crystalline $Fe_3O_4$ particles are covered with oleic acid and thus, dispersed well in a non-polar solvent such as hexane or toluene.

The nano-sized crystalline particles synthesized by using an organic solvent are nano-sized crystalline particles which are finely controlled in particle size and uniformed in particle diameter under the state of monodispersity. Therefore, the nano-sized crystalline particles are expected as the application for medical and/or biotechnology field as described in Patent Reference 1 (JP-A 10-503281 (KOHYO)), Patent Reference 2 (JP-A 2000-507197 (KOHYO)) and Patent Reference 3 (JP-A 2006-502572 (KOHYO)). The particles to be used in the medical and/or biotechnology field are normally used in the state of dispersion in a polar solvent such as a water. However, the nano-sized particles synthesized as described above can be dispersed well in a non-polar solvent, but not dispersed well in the polar solvent such as the water because the surfaces of the synthesized nano-sized particles are covered with aliphatic acid having long alkyl chain such as oleic acid.

As a method for substituting the aliphatic acid covering at the surfaces of the nano-sized particles with another surface covering suitable for the dispersion in the water, Non-patent Reference 1 discloses that aminoundecanoic acid tetramethylammonium as amphiphilic molecule is added and agitated in a hexane solvent where the hydrophobic $Fe_3O_4$ nano-sized particles covered with the oleic acid are dispersed so that the oleic acid is released from the surfaces of the $Fe_3O_4$ nano-sized particles, thereby producing hydrophilic $Fe_3O_4$ nano-sized particles.

In this way, in order to change the surface covering for the aliphatic acid-covering particles with a new covering by mixing and agitating the aliphatic acid-covering particles and a new surface covering material in a non-polar solvent, both conditions are required to be satisfied: One condition is that the new surface covering material can be solved in the non-polar solvent and the other condition is that the displacement reaction of the aliphatic acid surface covering by the new surface covering material can be conducted. In the case that the nano-sized particles are employed in the medical and/or biochemical field, the new surface covering material is required to be selected in view of the biocompatibility. In this point of view, even though the new surface covering material has the biocompatibility and thus, preferable for the substitution, the new surface covering material cannot be employed if the new surface covering material does not satisfy both of the conditions as described above. For example, it is very preferable that the nano-sized particles are covered with citric acid as disclosed in Patent Reference 4 (JP-A 2006-282582 (KOKAI)), but that the surface covering for the nano-sized particles formed according to Non-patent Reference 1 is substituted with the citric acid surface covering is not known.

Also, non-patent Reference 3 (J. Am. Chem. Soc. 2005, 127, p. 5732-5733) has reported that if the hydrophobic surface covering, which is formed through the thermal dissolution of iron acetylacetonato complex salt in an organic solvent, for the ferrite nano-sized particles is substituted with hydrophilic dimercaptosuccine acid surface covering, the intended hydrophilic surface covering ferrite nano-sized particles can be obtained which are suitable for the use in a living body. In non-patent Reference 3, the dimercaptosuccine acid is selected as a new surface covering material satisfying two conditions that the new surface covering material can be solved in the non-polar solvent and the displacement reaction of the aliphatic acid surface covering by the new surface covering material is conducted. As the result from that the aliphatic acid surface covering is practically substituted with the dimercaptosuccine acid surface covering, it was turned out that the dimercaptosuccine acid surface covering gradually solves the ferrite nano-sized particles. Namely, the nano-sized particles covered with dimercaptosuccine acid surface covering has a problem of chemical unstability.
Patent Reference 1: JP-A 10-503281 (KOHYO)
Patent Reference 2: JP-A 2000-507197 (KOHYO)
Patent Reference 3: JP-A 2006-502572 (KOHYO)
Patent Reference 4: JP-A 2006-282582 (KOKAI)
Non-patent Reference 1: J. Am. Chem. Soc. 2004, 126, p. 273-279
Non-patent Reference 2: Nat. Mater. 2004, 3, P. 891-895
Non-patent Reference 3: J. Am. Chem. Soc. 2005, 127, p. 5732-5733

DISCLOSURE OF THE INVENTION

Problem to be Solved by the Invention

As described above, since the inorganic particles such as ferrite particles synthesized in the organic solvent and finely controlled in particle size exhibit hydrophobicity because the surface aliphatic acid covering is conducted for the inorganic particles, the inorganic particles are not suitable for the dispersion in the polar solvent such as the water. In this point of view, although it is desired that the surface aliphatic acid covering is substituted with other various surface coverings suitable for the dispersion in the polar solvent, the substitution with the various surface coverings for the surface aliphatic acid covering cannot be conducted because of the above-described restriction for the surface covering substitution as of now.

It is an object of the present invention to provide a process for production of surface covering inorganic particles where the surface aliphatic acid covering for the inorganic particles are substituted with various surface covering materials suitable for the dispersion in a polar solvent and to provide the surface covering inorganic particles through the process production.

Technical Solution

The inventors paid attention to the fact that in the substituting method of the particle surface covering, the release of aliphatic acid and the covering of surface covering material suitable for the dispersion in the polar solvent occur simultaneously. In this point of view, the inventors separated the releasing process of the aliphatic acid and the covering process of the surface covering material in order to pursue the possibility of the solution for the conventional problem and thus, studied the possibility from various points of view.

As the result of the intense study for the possibility from various points of view, the inventors have conceived that a series of materials typified by thiomalic acid as followed can be substituted for the surface aliphatic acid of the particle surfaces in the non-polar solvent and cover the particle surfaces under good condition while the series of materials can be easily released from the particle surfaces in the polar solvent.

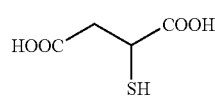
(Chemical formula 1)

Therefore, the inventors have conceived that the intended process of obtaining the surface covering particles is separated into two processes of releasing the aliphatic acid and covering the intended surface covering material. Namely, the series of materials typified by the thiomalic acid are used as temporal covering materials respectively so as to release the aliphatic acid from the particle surfaces and cover the particle surfaces through the substitution of the series of materials for the aliphatic acid, and subsequently, the temporal covering is substituted with an intended covering material. In this point of view, the inventors had much studied on the above-idea.

As a result, it was turned out that the temporal covering material is add into and reacted with a dispersion solution which is obtained by dispersing the aliphatic acid covering inorganic particles in the non-polar solvent so that the aliphatic acid can be released from the surfaces of the inorganic particles and then, the temporal material covering inorganic particles can be obtained through the substitution of the temporal material for the aliphatic acid. Then, the temporal material covering inorganic particles are dispersed in the polar solvent such as the water so that an intended polar solvent dispersion covering material such as citric acid is added into and reacted with the thus obtained dispersion solution, thereby obtaining the intended inorganic particles with surface covering thereof. In this way, the inventors have conceived the present invention.

This invention relates to a process for production of surface covering inorganic particles, including: a covering step of temporal covering material wherein a temporal covering material is added to release an aliphatic acid covering from aliphatic acid covering inorganic particles which are dispersed in a non-polar solvent and substitute the aliphatic acid covering with the temporal covering material in the non-polar solvent, thereby obtaining inorganic particles covered with the temporal covering material; and a covering step of polar solvent dispersion covering material wherein the inorganic particles covered with the temporal covering material are dispersed in a polar solvent while a polar solvent dispersion covering material with dispersibility for the polar solvent is added into the polar solvent to substitute the temporal covering material with the polar solvent dispersion covering material, thereby obtaining inorganic particles covered with the polar solvent dispersion covering material.

According to the process for the production of the inorganic particles, first of all, the aliphatic acid covering for the inorganic particles is substituted with the temporal covering material in the non-polar solvent and then, the temporal covering material is substituted with the intended surface covering material in the polar solvent so that the intended surface covering inorganic particles can be obtained from the aliphatic acid covering inorganic particles. In the production process, since the aliphatic acid covering for the inorganic particles is first substituted with the temporal covering material in the non-polar solvent and the temporal covering material is substituted with the surface covering material in the hydrophilic solvent, the surface covering material can easily cover the inorganic particles through the substitution of the aliphatic acid covering even through the surface covering material does not exhibit affinity for the hydrophobic solvent, for example. According to the production process, the surface covering inorganic particles with uniform diameter size within an average diameter range of 3 nm to 40 nm can be obtained.

This invention also relates to surface covering inorganic particles covered with a polar solvent dispersion covering material, wherein a temporal covering material substitutes an aliphatic acid covering of aliphatic acid covering inorganic particles in a non-polar solvent to obtain inorganic particles covered with the temporal covering material, the temporal covering material being to be substituted with a polar solvent dispersion covering material in a polar solvent thereafter to be released and an average diameter of the inorganic particles being within a range of 3 nm to 40 nm; and the polar solvent dispersion covering material with dispersibility for the polar solvent substitutes the temporal covering material under the condition that the inorganic particles covered with the temporal covering material are dispersed in the polar solvent to release the temporal covering material from the inorganic particles, thereby obtaining the surface covering inorganic particles covered with the polar solvent dispersion covering material.

The surface covering inorganic particles can be obtained by substituting the aliphatic acid covering for the inorganic particles which are finely controlled in particle size and uniformed in particle diameter in the organic solvent containing the aliphatic acid with the covering of the polar solvent dispersion covering material. As of now, it is difficult to produce the inorganic particles which are covered with the polar solvent dispersion covering material and which are finely controlled in particle size and uniformed in particle diameter. According to the present invention, the surface covering inorganic particles as described above can be produced and thus, the function of the surface covering inorganic particles for various application fields can be enhanced. Also, various applications not realized as of now can be realized using the surface covering inorganic particles.

The surface covering inorganic particles surface-covered with magnetic particles within a particle size range of 3 nm to 10 nm can be used as positive contrast medium for a magnetic resonance imaging (MRI) apparatus so as to enhance the characteristics such as high contrast of the positive contrast medium in comparison with a conventional one. On the other hand, the surface covering inorganic particles which are made by surface-covering the magnetic particles within a particle size range of 10 nm to 40 nm can be used as negative contrast medium for the MRI apparatus so as to enhance the characteristics of the negative contrast medium in comparison with a conventional one. Moreover, the surface covering organic particles according to the present invention which are made by surface-covering the magnetic particles can be employed as excellent magnetic hyperthermia carriers or excellent magnetic separating carriers. The surface covering organic particles can be employed as excellent biosensor carriers. Here, the surface covering inorganic particles can be provided with another surface covering material in view of the use thereof and then, can be employed for the use.

This invention also relates to inorganic particles covered with a temporal covering material, wherein the temporal covering material substitutes an aliphatic acid covering of aliphatic acid covering inorganic particles in a non-polar solvent and is to be substituted with a polar solvent dispersion covering material in a polar solvent to be released from the inorganic particles.

If the inorganic particles covered with the temporal covering material is employed, the surface covering for the inorganic particles can be substituted and covered with a predetermined polar solvent dispersion covering material such as citric acid, thereby obtaining the surface covering inorganic particles covered with the intended covering material.

Advantageous Effect

According to the production process of the surface covering inorganic particles of the present invention, the aliphatic covering for the inorganic particles can be substituted with various polar solvent dispersion covering so that the inorganic particles under the monodispersity state in the polar solvent can be obtained. The surface covering inorganic particles are finely controlled in particle diameter so as to be useful in chemical industrial field or another industry field and very applicable for various fields such as medical field and biotechnology.

EXPLANATION OF NUMERALS

11 . . . aliphatic acid covering magnetic particles, 12 . . . ligand exchange reaction of particle surface in non-polar solvent, 13 . . . inorganic particles covered with temporal covering material, 14 . . . ligand exchange reaction of particle surface in polar solvent, 15 . . . surface covering magnetic particles

BEST MODE FOR CARRYING OUT THE INVENTION

Hereinafter, the present invention will be described in detail with reference to the drawings.

1) Substitution Covering Process

Figure 1:
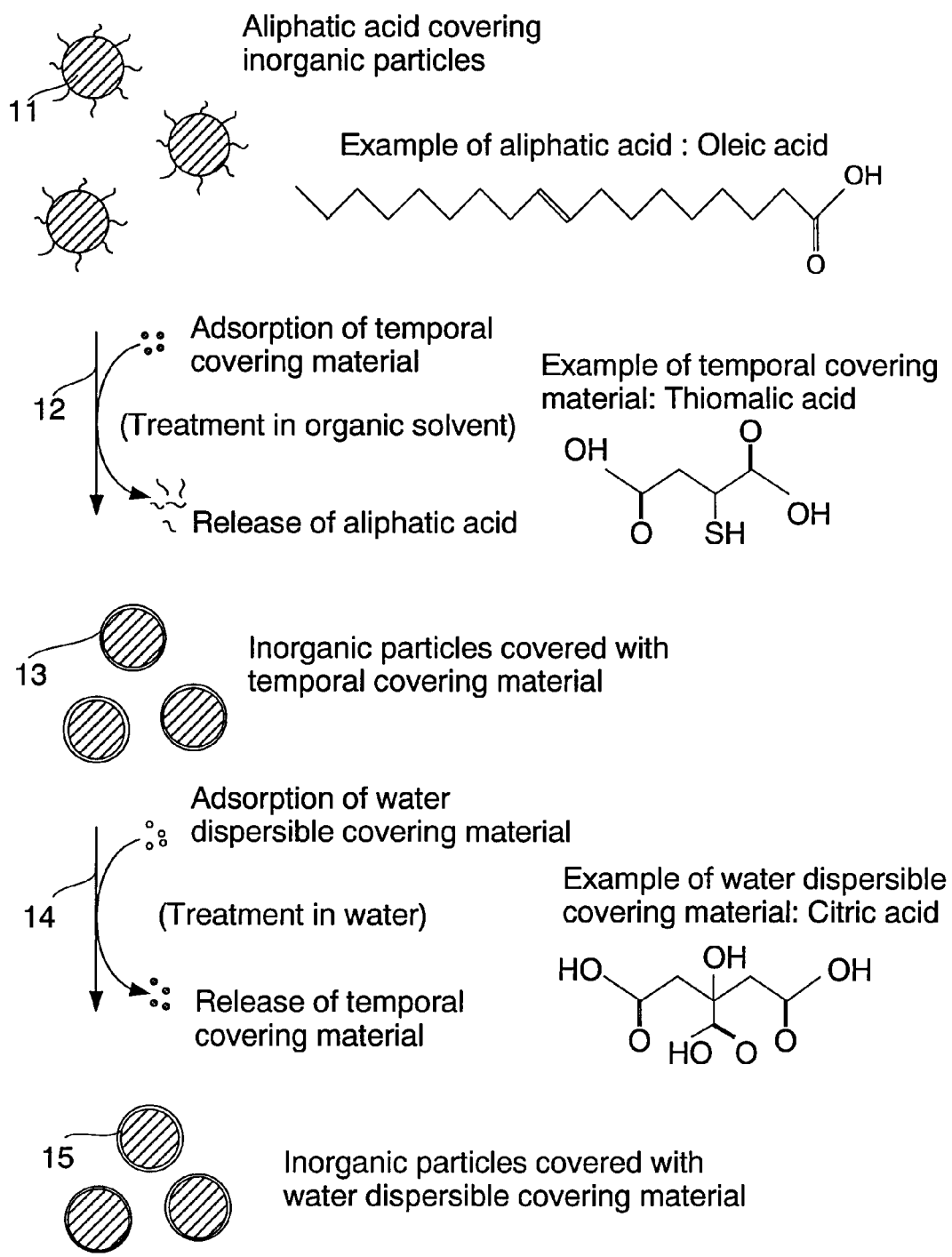
FIG. 1 is a view showing an embodiment relating to the production process of surface-covered magnetic particles according to the present invention.
Figure 2:
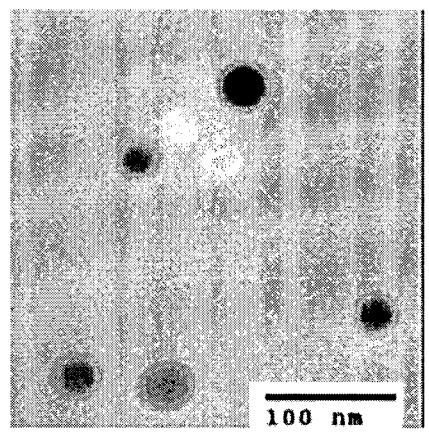
FIG. 2 is a TEM photograph relating to the ferrite particles in Example 8-1 where silica generated through the hydrolysis of tetraethoxysilane covers the ferrite particles surface-covered with citric acid.
Figure 3:
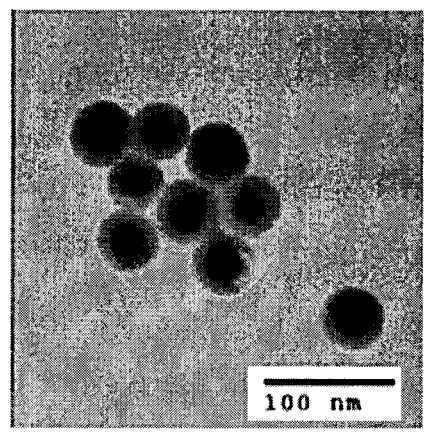
FIG. 3 is a TEM photograph relating to the ferrite particles in Example 8-2 where silica generated through the hydrolysis of tetraethoxysilane covers the ferrite particles surface-covered with citric acid.
Figure 4:
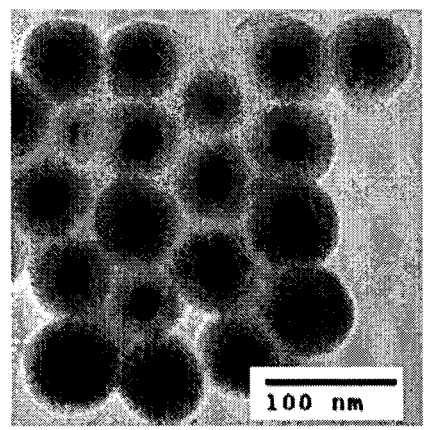
FIG. 4 is a TEM photograph relating to the ferrite particles in Example 8-3 where silica generated through the hydrolysis of tetraethoxysilane covers the ferrite particles surface-covered with citric acid.
Figure 5:
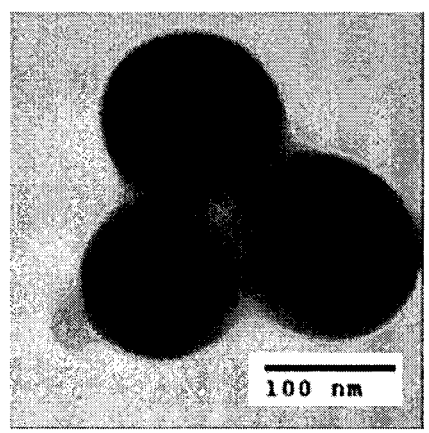
FIG. 5 is a TEM photograph relating to the ferrite particles in Example 8-4 where silica generated through the hydrolysis of tetraethoxysilane covers the ferrite particles surface-covered with citric acid.

FIG. 1 is a view showing an embodiment relating to the production process of surface-covered inorganic particles according to the present invention. As shown in FIG. 1, aliphatic acid covering inorganic particles covered with aliphatic acid of long chain such as oleic acid are dispersed in a non-polar solvent such as toluene. Then, a temporal covering material such as thiomalic acid is added into the thus obtained dispersion solution so that the aliphatic acid is released from the surfaces of the inorganic particles while the temporal covering material is adsorbed onto the surfaces of the inorganic particles through the covering material exchange reaction 12 at the surfaces of the inorganic particles in the non-polar solvent. Thereafter, the non-polar solvent, the aliphatic acid and the remaining temporal covering material not adsorbed are washed so as to obtain inorganic particles 13 covered with the temporal covering material.

Then, polar solvent dispersion covering material such as citric acid is solved in a polar solvent (e.g., MilliQ water as ultrapure water which is refined by means of reverse osmosis process and ultrafiltration process with the ion-exchange resin by use of the ultrapure water purifying apparatus made by Millipore Corporation, and the inorganic particles 13 covered with the temporal covering material are dispersed in the polar solvent so that the temporal covering material is released from the inorganic particles 13 through the covering material exchange reaction 14 at the surfaces of the inorganic particles 13 in the polar solvent as shown in FIG. 1 and the polar solvent dispersion covering material such as citric acid is adsorbed onto the surfaces of the inorganic particles 13. Thereafter, the inorganic particles 13 are washed to obtain the intended surface covering inorganic particles 15 surface-covered with the polar solvent dispersion covering material.

If a covering process of an additional polar solvent dispersion covering material (not shown) is conducted for the thus obtained surface covering inorganic particles 15 as occasion demands such that various polar solvent dispersion covering materials can additionally cover the inorganic particles 15, various surface covering inorganic particles with the respective surface characteristics can be provided suitable for various purposes of use.

In the present invention, the wording "surface covering" encompasses the state where the covering material covers the inorganic particle entirely or partially, or the state where a surface modification material modifies the surfaces of the inorganic particles.

2) Inorganic Particles

As the inorganic particles covered with the aliphatic acid may be exemplified ferrous ferrite particles such as magnetite particles and maghemite particles, various complex ferrite particles which are made by partially substituting the iron elements of the ferrous ferrite particles with metallic elements such as manganese (Mn) elements, cobalt (Co) elements, nickel (Ni) elements and zinc (Zn) elements, metallic particles such as iron particles, semiconductor particles such as ZnO particles, CdS particles and CdSe particles, and dielectric particles. These inorganic particles are finely controlled in particle diameter so that the aliphatic acid covering for the surfaces of the inorganic particles is substituted with the polar solvent dispersion covering material so as to obtain the surface covering inorganic particles which can be dispersed in the polar solvent such as a water.

The inorganic particles which are finely controlled in particle diameter can be formed by the process described in Non-patent Reference 1 or Non-patent citation No. 2 as descried above. For example, when iron triacetylacetone complex salt (Fe(acac)$_3$) is mixed with phenyl ether or benzyl ether containing oleic acid and oleylamine, and heated at a temperature within a range of 200° C. to 300° C., the nucleation for the inorganic particles can be well controlled and realized simultaneously for the inorganic particles so that the crystal growth for the inorganic particles can be progressed independently and simultaneously. As a result, nano-sized Fe$_3$O$_4$ particles can be obtained which are well controlled in particle diameter. Such complex ferrite particles as CoFe$_2$O$_4$ particles or MnFe$_2$O$_4$ particles can be generated in the same manner as described above if the iron acetylacetone complex salt is partially substituted with cobalt bisacetylacetone complex salt (Co(acac)$_2$) or manganese acetyl acetone complex salt (Mn(acac)$_2$). The average particle diameter of the thus obtained inorganic particles can be controlled within a range of 3 nm to 30 nm while the standard deviation of particle diameter distribution can be reduced to 15% or less for the average particle diameter. The standard deviation of particle diameter distribution can be controlled dependent on the particle growth condition so that the standard deviation of particle diameter distribution can be reduced to 10% or less, or 5% or less for the average particle diameter.

3) Polar Solvent

As the polar solvent used in the present invention may be typified water, particularly ultrapure water (e.g., MilliQ water) in view of the main use such as biotechnology use of the surface covering inorganic particles. Moreover, alcohols, N,N-dimethylformamide (DMF) and dimethylsulfoxide (DMSO) may be exemplified. A single polar solvent may be selected from the polar solvents listed above or a plurality of polar solvents may be selected from the polar solvents listed above thereafter to be mixed with one anther in use.

4) Temporal Covering Material

The temporal covering material used in the production process of the surface covering inorganic particles according to the present invention exhibits affinity for a non-polar solvent and covers the inorganic particles through the substitution of the aliphatic acid covering for the inorganic particles while the temporal covering material is substituted with an intended covering material to be released from the inorganic particles. As the temporal covering material, an organic material containing thiol group and carboxyl group which are both bonded in the molecules composing the organic material is preferable, and particularly, an organic material compound where the thiol group and the carboxyl group are bonded with one carbon atom as follows is more preferable.

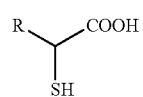

(Chemical formula 2)

Here, "R" represents alkyl group designated by C$_n$H$_{2n+1}$ (n=0 to 10), substituent alkyl group substituted by functional group, aryl group or substituent aryl group substituted by functional group. In order to develop the function of the temporal covering material, "n" is preferably set within a range of 0 to 6. As the functional group for the alkyl group and the aryl group may be exemplified amino group, carboxyl group, thiol group, sulfonic acid, phosphoric acid group, phosphorous acid group and hydroxyl group. Among the exemplified compounds, thiomalic acid can be more preferably employed and more, thioacetic acid or thiolactic acid can be preferably employed.

If the thiomalic acid is employed for the temporal covering material, the aliphatic acid covering for the surfaces of the inorganic particles can be sufficiently released in the non-polar solvent, thereby obtaining the intended inorganic particles covered with the thiomalic acid. The temporal covering of the thiomalic acid for the surfaces of the inorganic particles can be easily substituted in the polar solvent so that the intended surface covering inorganic particles of which the particle surfaces are substituted with the polar solvent dispersion covering material such as citric acid can be obtained.

As the temporal covering material in the production process of the surface covering inorganic particles of the present invention, such a compound as containing amino group, thiol group and ester group or containing amino group, sulfonic acid group and carboxyl group can be employed. As the compound may be employed at least one selected from the group consisting of L-cysteine methylester hydrochloride,

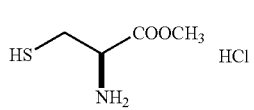

(Chemical formula 3)

L-cysteine ethylester hydrochloride,

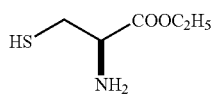
(Chemical formula 4)

and L-cysteic acid.

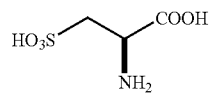
(Chemical formula 5)

Moreover, dithiothreitol containing two thiol groups and two hydroxyl group in one of the molecules composing the dithiothreitol may be employed.

As the temporal covering material in the production process of the surface covering inorganic particles of the present invention, aromatic monocyclic hydrocarbon or condensed polycyclic hydrocarbon which contain sulfonate or sulfate may be employed. As the compound may be exemplified 1-amino-8-naphthol-3,6-sodium disulfonate

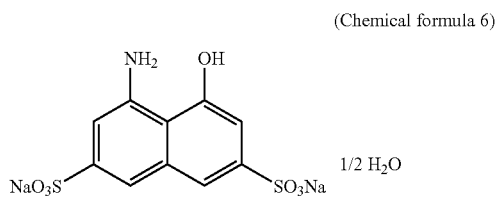
(Chemical formula 6)

Particularly, since the 1-amino-8-naphthol-3,6-sodium disulfonate can sufficiently substitute the aliphatic acid of the surfaces of the inorganic particles and thus, cover the inorganic particles, the 1-amino-8-naphthol-3,6-sodium disulfonate is a particularly preferable temporal covering material so as to obtain the surface covering inorganic particles in the polar solvent under the monodispersity state.

As the temporal covering material in the production process of the surface covering inorganic particles of the present invention, meso-2,3-dimercaptosuccinic acid as a compound containing thiol group

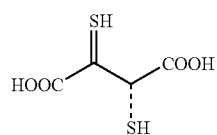
(Chemical group 7)

may be employed. In the case that the meso-2,3-dimercaptosuccinic acid is employed as the temporal covering material, the solution of the inorganic particles by the temporal covering material can be suppressed by restricting the covering period of time of the temporal covering material and substituting the temporal covering material with the covering of the polar solvent dispersion covering material.

5) Polar Solvent Dispersion Covering Material

In the production process of the surface covering inorganic particles according to the present invention, the polar solvent dispersion covering material is a material which substitutes the temporal covering material so as to cover the inorganic particles and thus, render the inorganic particles hydrophilic. As the polar solvent dispersion covering material, various polar solvent dispersion covering materials can be employed for the purpose of use of the inorganic particles. In medical field and biochemical field, particularly, various polar solvent dispersion covering materials in view of the biocompatibility may be employed. For example, as polycarboxylic acid containing hydroxyl group, maleic acid, citric acid and tartaric acid may be employed. As polycarboxylic acid containing amino group, asparatic acid and glutamic acid may be employed.

Among these polar solvent dispersion covering materials, the citric acid with smaller molecular weight has good adsorption for the surfaces of the inorganic particles and thus, particularly suitable for the covering for the surfaces of the nano-sized particles. Therefore, the inorganic particles covered with the citric acid can be employed for various uses as they are. Moreover, the inorganic particles are covered with the citric acid and then, also covered with another material for the purpose of use.

As the polar solvent dispersion covering material may be exemplified an organic material containing at least one functional group selected from the group consisting of carboxyl group, hydroxyl group, sulfonic acid group, thiol group, phosphoric acid group, carboxylic acid group, hydroxide, sulfonate, thiol salt, phosphate, silanediol and silanetriol. Moreover, a polymer containing at least one functional group selected from the group consisting of hydroxyl group, sulfonic acid group, carboxyl group and phosphoric acid group. As the polymer may be exemplified a compound or a derivative thereof containing phenolic hydroxyl group such as catechol and salicylic acid. As a compound containing amino acid may be employed oligopeptide and polypeptide with relatively small molecular weight or giant molecule such as protein. Moreover, a compound containing thiol group such as cysteine, a compound containing sulfonic acid group such as cystetic acid, a compound containing silanetriol may be employed. Furthermore, nucleic acid, derivative of nucleic acid, dextran, polyvinyl alcohol, polyacrylic acid, polyaspartic acid, polyglutamic acid, polylysine, alginic acid, hyaluronic acid, collagen and derivative of collagen may be employed.

6) Additional Surface Covering

In the present invention, after the inorganic particles are covered with the covering material such as the citric acid, the inorganic particles may be covered with an additional polar solvent dispersion covering material so as to obtain the inorganic particles covered with the surface covering material for the purpose of use. For example, the inorganic particles may be covered with the additional polar solvent dispersion covering material such as polyethylene glycol, as occasion demands, containing such a functional group as amino terminal group and/or thiol terminal group, or polypropyrene glycol, as occasion demands, containing such a functional group as amino terminal group and/or thiol terminal group. In the compound such as the polyethylene glycol and polypropylene glycol having the amino terminal group or the like, if the amino group is reacted with the carboxyl group of citric acid to form amide bond, the thus obtained compound has no electric charge in the polar solvent such as water. Therefore, the additional covering can iron out the problem that the inorganic particles are trapped by the electric charge in reticuloendothelium system (RES) tissue.

For example, the inorganic particles are covered with the citric acid or the like and then, covered with silica formed through the reaction with tetraethoxysilane.

The surface covering for the inorganic particles may be conducted by substituting the surface covering material such as the citric acid with an appropriate compound. According to the production process, the uniformity and dispersibility of the covered inorganic particles can be enhanced. If the bioactive function is applied to the surfaces of the inorganic particles, the covered inorganic particles can be preferably employed as MRI contrast medium or carriers in biosensor, for example.

In a compound such as polyethylene glycol and polypropylene glycol containing the functional groups such as amino groups at both terminals thereof, even though the amino group at one terminal is reacted with the carboxyl group of the citric acid, the amino group at the other terminal remains so that the remaining amino group has electric charge in the water. In the case that the compound such as polyethylene glycol and polypropylene glycol containing the functional groups such as amino groups at both terminals thereof is employed as the covering material, the amino group at one terminal is reacted with the carboxyl group to form the amide bond and the amino group at the other terminal is bonded with bioactive material.

7) Application of Surface Covering Inorganic Particles

The inorganic particles covered with the biocompatible organic material, which are produced according to the present invention, can be employed for various uses utilizing the characteristics thereof.

The magnetic particles covered with the polar solvent dispersion covering material which can be produced according to the present invention, uniformed in particle size and have good dispersibility can exhibit excellent performance as MRI contrast medium. The covered magnetic particles, the magnetic particles having an average diameter of 10 nm or less, e.g., within a range of 3 nm to 10 nm and a standard deviation of particle diameter distribution of 15% or less for the average diameter, have larger relaxation constants $R_1$ and $R_2$ in comparison with conventional magnetic particles and set the value of $R_2/R_1$ to almost one. The relaxation constants $R_1$ and $R_2$ can be represented as the inverse numbers of longitudinal relaxation time $T_1$ and transverse relation time $T_2$, respectively. In this way, the positive contrast of high signal can be realized in MRI than ever. On the other hand, since the magnetic particles with an average diameter within a range of 10 nm to 40 nm and with a standard deviation of particle diameter distribution of 15% or less for the average diameter which are produced according to the present invention have a larger relaxation constant $R_2$, the magnetic particles can exhibit excellent performance as negative contrast medium. If the thus produced magnetic particles are covered with the biocompatible organic material such as polyethylene glycol under the monodispersity state, the trapping for the particles in RES can be prevented. In this way, the ferrite particles covered with the polyethylene glycol is useful as MRI contrast medium in nuclear magnetic resonance diagnosis.

The magnetic particles covered with the polar solvent dispersion covering material which are produced according to the present invention and uniformed in particle size are useful for magnetic hyperthermia carriers. In magnetic hyperthermia, it is known that the magnetic heat quantity by means of high frequency heating depends on the primary particle diameter. In order to obtain the magnetic heat quantity, it is desired that the magnetic particles are rendered the monodispersity state without the aggregation of the magnetic particles. Since the surface covering magnetic particles with an average diameter within a range of 3 nm to 40 nm and with a standard deviation of particle diameter distribution of 15% or less for the average diameter absorb the energy of electromagnetic wave to generate heat and prevent the trapping for the surface covering magnetic particles themselves in RES, the surface covering magnetic particles are particularly preferable for the magnetic hyperthermia carriers. The sizes of the magnetic particles are preferably set within a range of 10 nm to 30 nm in order to obtain excellent hyperthermia performances.

The magnetic particles covered with the polar solvent dispersion covering material are useful for biosensor carriers by fixing substance recognition base material on the magnetic particles. The substance recognition base material having sensor function may be fixed on the inorganic particles via the polar solvent dispersion covering material or directly cover the inorganic particles. If the ferrite magnetic particles are employed as the inorganic particles of the present invention, the magnetic response biosensor can be obtained. Furthermore, the quantum dots which are produced by surface-covering the inorganic particles such as ZnO with the biocompatible material such as the polyethylene glycol are useful for fluorescent carriers.

Nucleic acid (DNA, RNA, PNA), peptide or derivative thereof may be bonded as bioactive material onto the surface covering inorganic particles produced according to the present invention. The thus obtained inorganic particles may be employed for various diagnosis and medical treatment. The ferrite magnetic particles as the inorganic particles can be employed for various uses such as magnetic separation carriers, magnetic sensor probes, MRI contrast medium or magnetic hyperthermia carriers utilizing the magnetic property of the magnetic particles.

EXAMPLES

Example 1

Use of Thiomalic Acid as Temporal Covering Material

First, 5 ml or more of 2-propanol (made by Kishida Chemical Co. Ltd.) was added into 180 mg of octadecene suspension containing oleic acid covering ferrite particles with an average diameter of about 8 nm which are finely controlled in particle diameter to aggregate the ferrite particles. Then, the ferrite particles were magnetically recovered so that the supernatant liquid was disposed. The above-described process was repeated three times using 10 ml of 2-propanol. The octadecene suspension containing the oleic acid covering ferrite particles was obtained as follows. Namely, iron chloride was reacted with sodium oleic acid to prepare iron-oleic acid complex salt, which was mixed with oleic acid and solved in octadecene at room temperature. Then, the thus obtained solution was heated to 320° C. for 90 minutes and reacted at the same temperature for 30 minutes, and cooled down to room temperature.

The 2-propanol was removed and 16 ml of toluene was added to disperse the particles in the solution. Then, 0.324 g of thiomalic acid (made by TOKYO CHEMICAL INDUSTRY CO., LTD., Mw=150.15) was solved in 4 ml of dimethylsulfoxide, and then, added into the thus obtained toluene dispersion solution as described above, and sonicated (supersonic-treated) for 4 hours.

Then, 10 ml of 2-methoxyethanol (made by Kishida Chemical Co. Ltd.) was added to aggregate the ferrite particles in the solution. Then, the ferrite particles were magnetically recovered so that the thus obtained supernatant solution was disposed. The ferrite particles were washed by 2-methoxyethanol so as to remove the isolated oleic acid and the excess thiomalic acid, thereby producing thiomalic acid covering ferrite particles.

Then, 0.415 g of citric acid (anhydride, made by Kishida Chemical Co. Ltd., Mw=192.13) was solved in a MilliQ water so that the pH value of the thus obtained citric acid aqueous solution was adjusted to the pH value of 7 by using 6M NaOH solution and the final volume of the citric acid aqueous solution was set to 20 ml. The citric aqueous solution was added to the thiomalic acid covering ferrite particles and sonicated for 4 hours.

Then, 10 ml of 1,4-dioxane (made by Kishida Chemical Co. Ltd.) was added to aggregate the ferrite particles. The ferrite particles were magnetically recovered so that the thus obtained supernatant solution was disposed. Then, the recovered ferrite particles were washed three times by 10 ml of 1,4-dioxane so as to remove the isolated thiomalic acid and the excess citric acid.

Then, 1,4-dioxane was added to aggregate the ferrite particles so that the thus obtained supernatant solution was disposed. Then, 10 ml of MilliQ water was added to disperse the ferrite particles and the thus obtained dispersion solution was dialyzed for 12 hours and more using MilliQ water. The thus obtained dispersion solution was penetrated through a filter (Millipore Corporation, Millex GP Filter unit 0.22 µm) to obtain citric acid covering ferrite particles dispersion solution.

When the diameters in water of the ferrite particles in the dispersion solution were measured by dynamic light scattering method, the diameters in water fell within a range of 10.5±1.3 nm. Moreover, when the ferrite particles were observed by transmission electron microscope (TEM) so as to measure the average diameter thereof, the average diameter of the ferrite particles was about 8 nm. The particle weight distribution of the ferrite particle dispersion solution became maximum around 8 nm. In the dispersion solution, it was turned out that the number of the particles with the weight distribution of about 8 nm under monodispersity state became maximum and the particles were dispersed in the solution.

Example 2

Use of 1-amino-8-naphtol-3,6-sodium Disulfonate as Temporal Covering Material

The surface covering for the ferrite particles was conducted in the same manner as Example 1 to obtain the citric acid covering ferrite particle dispersion solution except that 0.737 g of 1-amino-8-naphtol-3,6-sodium disulfonate (made by TOKYO CHEMICAL INDUSTRY CO., LTD., Mw=341.29) was employed as the temporal covering material.

When the diameters in water of the ferrite particles in the dispersion solution using the 1-amino-8-naphtol-3,6-sodium disulfonate as the temporal covering material were measured by dynamic light scattering method, the diameters in water fell within a range of 8.0±0.9 nm. Moreover, when the ferrite particles were observed by transmission electron microscope (TEM) so as to measure the average diameter thereof, the average diameter of the ferrite particles was about 8 nm. The particle weight distribution of the ferrite particle dispersion solution became maximum around 8 nm so that it was turned out that the particles with the weight distribution of about 8 nm were under monodispersity state as Example 1.

Example 3

Use of meso-2,3-dimercaptosuccinic Acid as Temporal Covering Material

The surface covering for the ferrite particles was conducted in the same manner as Example 1 obtain the citric acid covering ferrite particle dispersion solution except that 0.394 g of meso-2,3-dimercaptosuccinic acid (made by TOKYO CHEMICAL INDUSTRY CO., LTD., Mw=182.22) was employed as the temporal covering material. The dispersion solution of the ferrite particles covered with the meso-2,3-dimercaptosuccinic acid was colored and the iron ions of the ferrite particles were partially solved in the dispersion solution.

When the diameters in water of the ferrite particles in the dispersion solution using the meso-2,3-dimercaptosuccinic acid as the temporal covering material were measured by dynamic light scattering method, the diameters in water fell within a range of 9.0±4.6 nm. Moreover, when the ferrite particles were observed by transmission electron microscope (TEM) so as to measure the average diameter thereof, the average diameter of the ferrite particles was about 8 nm. The particle weight distribution of the ferrite particle dispersion solution became maximum around 8 nm so that it was turned out that the particles with the weight distribution of about 8 nm were under monodispersity state as Example 1.

Example 4

Use of Other Several Materials as Temporal Covering Materials

The surface covering for the ferrite particles was conducted in the same manner as Example 1 to obtain the citric acid covering ferrite particle dispersion solution except that thioglycolic acid (made by TOKYO CHEMICAL INDUSTRY CO., LTD.) represented by chemical formula 8,

(Chemical formula 8)

thiolactic acid (made by TOKYO CHEMICAL INDUSTRY CO., LTD.) represented by chemical formula 9,

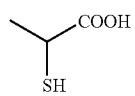

(Chemical formula 9)

3-mercaptopropionic acid (made by TOKYO CHEMICAL INDUSTRY CO., LTD.) represented by chemical formula 10,

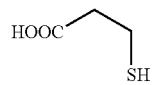

(Chemical formula 10)

malonic acid (made by TOKYO CHEMICAL INDUSTRY CO., LTD.) represented by chemical formula 11,

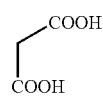

(Chemical formula 11)

succinic acid (made by TOKYO CHEMICAL INDUSTRY CO., LTD.) represented by chemical formula 12,

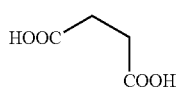
(Chemical formula 12)

and 1-2 ethanedithiol (made by TOKYO CHEMICAL INDUSTRY CO., LTD.) (Comparative Example) represented by chemical formula 13,

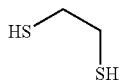
(Chemical formula 13)

are employed instead of the thiomalic acid, respectively.

When the diameters in water of the ferrite particles in the dispersion solution were measured by dynamic light scattering method, the diameters in water fell within a range of 10.1±5.7 nm, 9.2±5.5 nm, 8.1±4.2 nm, 16.3±6.9 nm, 47.1±11.8 nm, 22.5±12.7 nm or 199.6±31.8 nm for the thioglycolic acid, the thiolactic acid, the 3-mercarptopropionic acid, the malonic acid, the succinic acid or the 1-2 ethanedithiol (Comparative Example). From the result, it was turned out that when the thioglycolic acid, the thiolactic acid and the 3-mercarptopropionic acid where both of thiol group and carboxyl group are bonded with one carbon atom were employed as the temporal covering materials, respectively, the respective diameters in water were close to the inherent diameters in water of the ferrite particles, so that the thioglycolic acid, the thiolactic acid and the 3-mercarptopropionic acid can be employed as the thiomalic acid.

Example 5

Use of L-Cysteic Acid as Temporal Covering Material

The surface covering for the ferrite particles was conducted in the same manner as Example 1 to obtain the citric acid covering ferrite particle dispersion solution except that 0.365 g of L-cysteic acid (made by NACALAI TESQUE, INC., Mw=169.16) was employed as the temporal covering material.

When the diameters in water of the ferrite particles in the dispersion solution using the L-cysteic acid as the temporal covering material were measured by dynamic light scattering method, the diameters in water fell within a range of 57.4±10.4 nm. Moreover, when the ferrite particles were observed by transmission electron microscope (TEM), the primary diameter of the ferrite particles was about 8 nm. The particle weight distribution showed that the plurality of ferrite particles were aggregated and dispersed in the solution.

Example 6

Use of L-cystein Methylester Hydrochloride as Temporal Covering Material

The surface covering for the ferrite particles was conducted in the same manner as Example 1 to obtain the citric acid covering ferrite particle dispersion solution except that 0.371 g of L-cystein methylester hydrochloride (made by TOKYO CHEMICAL INDUSTRY CO., LTD., Mw=171.65) was employed as the temporal covering material.

When the diameters in water of the ferrite particles in the dispersion solution using the L-cystein methylester hydrochloride as the temporal covering material were measured by dynamic light scattering method, the diameters in water fell within a range of 43.4±7.8 nm. Moreover, when the ferrite particles were observed by transmission electron microscope (TEM), the primary diameter of the ferrite particles was about 8 nm. The particle weight distribution showed that the plurality of ferrite particles were aggregated and dispersed in the solution.

Example 7

Use of L-cystein Ethylester Hydrochloride as Temporal Covering Material

The surface covering for the ferrite particles was conducted in the same manner as Example 1 to obtain the citric acid covering ferrite particle dispersion solution except that 0.401 g of L-cystein ethylester hydrochloride (made by TOKYO CHEMICAL INDUSTRY CO., LTD., Mw=185.67) was employed as the temporal covering material.

When the diameters in water of the ferrite particles in the dispersion solution using the L-cystein ethylester hydrochloride as the temporal covering material were measured by dynamic light scattering method, the diameters in water fell within a range of 53.4±8.9 nm. Moreover, when the ferrite particles were observed by transmission electron microscope (TEM), the primary diameter of the ferrite particles was about 8 nm. The particle weight distribution showed that the plurality of ferrite particles were aggregated and dispersed in the solution.

In this way, the surface covering particles can be produced which can be dispersed in a polar solvent such as water by substituting the aliphatic acid covering the inorganic particles with the temporal covering material and then, also substituting the temporal covering material with the polar solvent dispersion covering material such as nitric acid.

Example 8

Use of Polyacrylic Acid as Protic Solvent Dispersion Covering Material

A dispersion solution containing polyacrylic acid covering ferrite particles was prepared in the same manner as Example 1 except that oleic acid covering ferrite particles with an average diameter of 4 nm were employed as the inorganic particles, and the thiomalic acid was employed as the temporal covering material, and polyacrylic acid

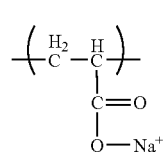
(Chemical formula 14)

was employed as the protic solvent dispersion covering material. When the diameters in water of the ferrite particles in the dispersion solution were measured by dynamic light scattering method, the diameters in water fell within a range of 7.8±1.0 nm. Moreover, when the ferrite particles were observed by transmission electron microscope (TEM), the primary diameter of the ferrite particles was about 4 nm. The particle weight distribution showed that the plurality of ferrite particles were aggregated and dispersed in the solution.

The measurement results for the particle covering dispersion solutions produced in Examples 1 to 7 were all listed at Table 1.

TABLE 1

| Temporal covering material | Polar solvent dispersion covering material | Primary diameter (TEM) | Diameter in water (dynamic light scattering method) |
|---|---|---|---|
| Thiomalic acid | Citric acid | 8 nm | 8.1 ± 4.2 nm |
| 1-amino-8-naphtol-3, 6-sodium disulfonate | Citric acid | 8 nm | 8.0 ± 0.9 nm |
| Meso-2, 3-dimercaptosuccinic acid | Citric acid | 8 nm | 9.0 ± 4.6 nm |
| Thioglycolic acid | Citric acid | 8 nm | 10.1 ± 5.7 nm |
| Thiolactic acid | Citric acid | 8 nm | 9.2 ± 5.5 nm |
| 3-MPA | Citric acid | 8 nm | 16.3 ± 6.9 nm |
| Malonic acid | Citric acid | 8 nm | 47.1 ± 11.8 nm |
| Succinic acid | Citric acid | 8 nm | 22.5 ± 12.7 nm |
| 1,2-ethanediol (Comparative Example) | Citric acid | 8 nm | 199.6 ± 31.8 nm |
| L-cysteic acid | Citric acid | 8 nm | 57.4 ± 10.4 nm |
| Salt of L-cystein methylester salt acid | Citric acid | 8 nm | 43.4 ± 7.8 nm |
| Salt of L-cystein ethylester salt acid | Citric acid | 8 nm | 53.4 ± 8.9 nm |
| Thiomalic acid | Polyacrylic acid | 4 nm | 7.8 ± 1.0 nm |

Example 9

Production of Tetraethoxysilane Covering Particles

The citric acid covering ferrite particles were prepared in the same manner as Example 1, and dispersed in a mixed solution of ethanol and water (ethanol:water=1:1 in volume ratio).

Then, tetraethoxysilane (TEOS, $Si(OC_2H_5)_4$) was added into the thus obtained dispersion solution, and 28% ammonia aqueous solution was added and reacted at room temperature to cover the surfaces of the nitric acid covering ferrite particles with silica generated through the hydrolysis of the TEOS. Four kinds of nitric acid covering ferrite particles were prepared by changing the reactive condition such that the covering amount of silica became different for each kind of nitric acid covering ferrite particles. The amount of the magnetic particles, the amount of the TEOS, the amount of the ammonia and the reactive temperature were listed as the covering reactive condition at Table 2 with the covering results of the silica covering ferrite particles.

TABLE 2

| | Amount of Magnetic particles (Fe conversion) | Amount of TEOS | Amount of ammonia | Reaction time | Covering thickness |
|---|---|---|---|---|---|
| Example 8-1 | 36 µmol | 5 µmol | 1.5 mmol | 7 hours | 5 nm |
| Example 8-2 | 36 µmol | 50 µmol | 1.5 mmol | 7 hours | 10 nm |
| Example 8-3 | 3.6 µmol | 20 µmol | 6.0 mmol | 2 hours | 20 nm |
| Example 8-4 | 3.6 µmol | 200 µmol | 6.0 mmol | 2 hours | 45 nm |

The produced silica covering and nitric covering ferrite particles were recovered and the covering states for the covering ferrite particles were examined by means of TEM.

FIGS. 2 to 5 are TEM photographs for the states where the nitric acid covering ferrite particles were covered with the silica in Examples 8-1 to 8-4, respectively. It is recognized from these photographs that the covering ferrite particles were uniformed in particle diameter and a single ferrite particle existed in the inside of the corresponding covering ferrite particle, and the silica covering is formed in a uniform thickness around the single ferrite particle. Moreover, it was turned out from the results that the thickness of the silica covering generated through the hydrolysis was able to be finely controlled by selecting the reactive condition.

The silica covering thicknesses measured by the observation using microscope were also listed at Table 2 in contrast with the covering reactive condition.

Example 10

Contrast Effect as MRI Contrast Medium

The nitric acid covering iron ferrite nanoparticles were prepared as magnetic particles with respective average diameters of 4 nm, 8 nm and 20 nm in the same manner as Example 1. Then, the contrast effect as MRI contrast medium in nuclear magnetic resonance diagnosis was examined for the nitric acid covering iron ferrite nanoparticles and compared with the contrast effect of Resovist (registered mark) used as negative contrast medium for clinical use. The NMR analyzer minispec 0.47T (Bruker Optics Inc.) was used as a measuring apparatus, and then, the nanoparticles were dispersed in the MilliQ water to measure the longitudinal relaxation time $T_1$ and the transverse relaxation time $T_2$ by IR (inversion recovery) method and CPMG (Carr-Purcell-Meiboom-Gill) method. Then, the inverse numbers $R_1$ and $R_2$ for the longitudinal relaxation time $T_1$ and the transverse relaxation time $T_2$ were calculated respectively while the ratio ($R_2/R_1$) was calculated.

The measurement results in proton nuclear magnetic resonance relaxation for three kinds of nitric acid covering iron ferrite nanoparticles with the respective different average diameters were listed at Table 3. In comparison, the measurement result for Resovist used as the negative contrast medium was also listed at Table 3.

TABLE 3

| | $R_1$ value | $R_2$ value | $R_2/R_1$ value | Average primary particle diameter (nm) | Diameter in water (nm) |
|---|---|---|---|---|---|
| 4 nm citric acid covering particle | 10.5 | 18.3 | 1.74 | 4.0 | 4.2 |
| 8 nm citric acid covering particle | 36.2 | 80.4 | 2.22 | 8.0 | 8.4 |
| 20 nm citric acid covering particle | 43.9 | 380 | 8.67 | 20.0 | 21 |
| Comparison: Resovist | 10.5 | 220 | 21.0 | 8.0 | 60 |

The ratio of $R_2/R_1$ is used as an index for the positive or negative contrast medium in MRI. Generally, when the ratio of $R_2/R_1$ becomes close to "1", a given contrast medium can be used as the positive contrast medium exhibiting the positive contrast.

The Resovist as the contrast medium for clinical use is used as the negative contrast medium exhibiting the negative contrast in MRI scans. Since the Resovist is introduced into a liver as soon as the Resovist is administered in the blood, the Resovist is utilized in order to visualize a tumor in the liver. Generally, since a contrast medium such as the Resovist is not introduced into the tumor, only the normal portions can be seen under the state of negative contrast in the MRI scans.

Moreover, the Gd-DTPA as a contrast medium for clinical use is a positive contrast medium exhibiting the positive contrast in the MRI scans. When the Gd-DTPA is administered in the blood, the Gd-DTPA is not introduced into a liver or another internal organ, but circulated in the blood vessels. Therefore, the Gd-DTPA is used as a blood vessel contrast. However, there is a problem that the Gd-DTPA is extravasated into the tissues from the blood vessels with time. In this point of view, such an MRI contrast medium as not extravasated into the tissues from the blood vessels and clearing the contrast between the blood vessels and the tissues is desired. Since it is known that an iron-based contrast medium can exhibit contrast effect at a small amount of contrast medium in comparison with the Gd-based contrast medium, the iron-based contrast medium capable of exhibiting the positive contrast is superior to the Gd-based contrast medium.

Referring to Table 3, since the ratios of $R_2/R_1$ of all kinds of iron ferrite particles are smaller than the ratio of $R_2/R_1$ of the Resovist, it is suggested that the nitric acid covering iron ferrite particles, produced according to the present invention, can be used as the positive contrast medium in comparison with the Resovist. Particularly, since the ratios of $R_2/R_1$ of the nitric acid covering iron ferrite particles with the respective average diameters of 4 nm and 8 nm are very close to "1", the nitric acid covering iron ferrite particles may be much promised as the positive contrast medium. Also, since the nitric acid covering iron ferrite particles are almost rendered the state of monodispersity, the nitric acid covering iron ferrite particles can be retained in the blood so as not to be introduced into the liver. Therefore, the nitric acid covering iron ferrite particles can be used for angiography. On the other hand, since the nitric acid covering iron ferrite particles with the average diameter of 20 nm have the very large $R_1$ and $R_2$, it is shown that the nitric acid covering iron ferrite particles can be used as the extremely effective contrast medium.

Example 11

Application as Magnetic Hyperthermia Carriers

If the magnetic particles, which are made by covering the surface covering magnetic particles produced according to the present invention with the surface solvent dispersion covering material, are employed as magnetic hyperthermia carriers, the magnetic particles can exhibit excellent characteristics as the magnetic hyperthermia carriers. The hyperthermia means a thermotherapy which selectively kills cancer cells by thermal treatment. As the heating means for the thermal treatment, conventionally, dielectric heating, which is conducted by the addition of a high frequency electric field from a high frequency electrode, would be employed. However, the dielectric heating results in heating the normal tissues by the dielectric loss. In the magnetic hyperthermia, in contrast, the magnetic particles are disposed at a portion to be heated and then, a high frequency magnetic field is applied to heat the portion using the dielectric loss of the magnetic particles. In the case that the portion contains cancer cells, if the magnetic particles are covered with the antibody specifically bonded with the cancer cells, the magnetic particles can be selectively applied to the cancer cells. In this way, the advantage of the hyperthermia that the portion to which the magnetic particles are disposed can be selectively heated and other normal portion to which the magnetic particles are not disposed cannot be heated can be exhibited.

If the dispersion solution of the magnetite particles with an average diameter within a range of 3 nm to 40 nm as the magnetic particles which are covered with the nitric acid and treated with polyethylene glycol or the dispersion solution of the thus obtained magnetite particles bonded with antibody is applied to the portion to be heated and a high frequency current of 900 kHz is flowed in a high frequency exciting coil to generate a high frequency magnetic field of about 50 Oe (3980 A/m), the dielectric loss can be effectively generated at the magnetite particles. In this way, the excellent magnetic hyperthermia can be conducted than ever.

Example 12

Application as Biosensor Carriers

In the present invention, if the inorganic particles are covered with substance recognition base material, biosensor carriers can be provided. If bioactive function is applied to the covering material, the surface covering inorganic particles preferable for the biosensor carriers can be obtained. The substance recognition base material may be fixed to the inorganic particles via the polar solvent dispersion covering material or directly cover the inorganic particles. If the ferrite particles are employed as the inorganic particles, the magnetic response biosensor carriers can be obtained.

Particularly, if the nucleic acid (DNA, RNA, PNA), peptide or derivative thereof is bonded with the surface covering inorganic particles, the inorganic particles bonded with the nucleic acid or the like can detect antigen. If the surface covering inorganic particles contain ferrite particles, the inorganic particles bonded with the nucleic acid or the like can detect the antigen by the measuring method of magnetic marker signal. The measurement of the magnetic maker signal can be conducted using a semiconductor hall sensor or a superconducting quantum interference device (SQUID). If the superconducting quantum interference device is employed, the magnetic detection can be conducted at high sensitivity.

Example 13

If the surface covering inorganic particles contain ferrite particles particularly with an average diameter within a range of 3 nm to 40 nm and a standard deviation of particle diameter distribution of 15% or less for the average diameter, the surface covering inorganic particles can exhibit excellent characteristics as magnetic separation carriers. If a specific antibody is bonded with the surface covering inorganic particles, the surface covering inorganic particles bonded with the specific antibody can be used for the separation and extraction of antigen using the property that the antibody can be specifically bonded with a specific antigen.

The surface covering inorganic particles bonded with the specific antibody are immersed in a liquid containing the antigen so that the antigen is bonded with the surface covering inorganic particles. Then, the magnetic separation process using magnetic field gradient is conducted for the surface covering inorganic particles to be separated and washed so as to separate the antigen from the surface covering inorganic particles. According to the process, the antigen can be separated and extracted more effectively.

INDUSTRIAL APPLICABILITY

If the covering for the aliphatic acid covering inorganic particles is substituted with a polar solvent dispersion material according to the present invention, the surface covering inorganic particles with good dispersibility for a polar solvent can be obtained. Particularly, since the covering for the aliphatic acid covering inorganic particles which are finely controlled in particle diameter can be substituted with the polar solvent dispersion material to obtain the surface covering inorganic particles with good dispersibility for the polar solvent. The surface covering inorganic particles, according to the present invention, are expected for various fields such as medical field and biotechnology field.

What is claimed is:

1. A process for production of surface covering inorganic particles, comprising:
adding, to a dispersion that comprises inorganic particles covered in an aliphatic acid, a temporal covering material to release the aliphatic acid from the inorganic particles and substitute the aliphatic acid with the temporal covering material, thereby obtaining inorganic particles covered with the temporal covering material;
dispersing the inorganic particles covered with the temporal covering material in a polar solvent, thereby obtaining a dispersion of inorganic particles covered with the temporal covering material; and
adding, to the dispersion of inorganic particles covered with the temporal covering material, a polar solvent dispersion covering material to substitute the temporal covering material with the polar solvent dispersion covering material, thereby obtaining inorganic particles covered with the polar solvent dispersion covering material,
wherein
said polar solvent dispersion covering material is citric acid.

2. The process as set forth in claim 1,
wherein the temporal covering material is a compound where both thiol group and carboxyl group are bonded with one carbon atom.

3. The process as set forth in claim 2,
wherein the compound is at least one selected from the group consisting of thiomalic acid, thiolactic acid and thioacetic acid.

4. A process for production of surface covering inorganic particles, comprising:
adding, to a dispersion that comprises inorganic particles covered in an aliphatic acid, a temporal covering material, to substitute the aliphatic acid with the temporal covering material, thereby obtaining inorganic particles covered with the temporal covering material;
dispersing the inorganic particles covered with the temporal covering material in a polar solvent, thereby obtaining a dispersion of inorganic particles covered with the temporal covering material; and
adding, to the dispersion of inorganic particles covered with the temporal covering material, a polar solvent dispersion covering material, to substitute the temporal covering material with the polar solvent dispersion covering material, thereby obtaining inorganic particles covered with the polar solvent dispersion covering material,
wherein the temporal covering material is at least one selected from the group consisting of L-cystein methylester, L-cystein ethylester, cysteic acid and a salt thereof.

5. The process as set forth in claim 1,
wherein the temporal covering material is dithiothreitol.

6. The process as set forth in claim 1,
wherein the temporal covering material is an aromatic monocyclic hydrocarbon or a condensed polycyclic hydrocarbon which comprises at least one functional group selected from the group consisting of a sulfonic acid group, a sulfonate, a sulfuric acid group and a sulfate.

7. The process as set forth in claim 6,
wherein the aromatic monocyclic hydrocarbon or condensed polycyclic hydrocarbon is 1-amino-8-naphtol-3, 6-disulfonic acid or a salt thereof.

8. The process as set forth in claim 1,
wherein the polar solvent dispersion covering material is a compound comprising a phenolic hydroxyl group or a derivative thereof.

9. The process as set forth in claim 1,
wherein the polar solvent dispersion covering material is an organic material comprising at least one functional group selected from the group consisting of a carboxyl group, a hydroxyl group, a sulfonic acid group, a thiol group, a phosphoric acid group, a carboxylate, a hydroxide, a sulfonate, a thiol salt, a phosphate, a silanediol and a silanetriol.

10. The process as set forth in claim 1,
wherein the polar solvent dispersion covering material is a polymer comprising at least one functional group selected from the group consisting of a hydroxyl group, a sulfonic acid group, a carboxyl group and a phosphoric acid group.

11. The process as set forth in claim 10,
wherein the polar solvent dispersion covering material is an aromatic material comprising a hydroxyl group.

12. The process as set forth in claim 1,
further comprising covering the inorganic particles covered with the polar solvent dispersion covering material with a second polar solvent dispersion material.

13. The process as set forth in claim 12,
wherein the second polar solvent dispersion covering material is silica generated through hydrolysis of tetraethoxysilane.

14. The process as set forth in claim 1,
wherein the inorganic particles are magnetic particles.

15. The process as set forth in claim 1,
wherein the polar solvent is water.

16. The process as set forth in claim 1,
wherein the temporal covering material is a compound where both thiol group and carboxyl group are bonded with one carbon atom and is represented by formula (2):

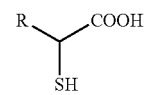

where R represents an alkyl group designated by $C_nH_{2n+1}$ with n=0 to 10, a substituent alkyl group substituted by a functional group, or an aryl group or a substituent aryl group substituted by functional group.

* * * * *